(12) United States Patent
Faizan et al.

(10) Patent No.: US 11,433,916 B1
(45) Date of Patent: Sep. 6, 2022

(54) SYSTEM TO GENERATE AN ALERT TO WAKE A DRIVER OF A VEHICLE AND A METHOD THEREOF

(71) Applicant: Mirza Faizan, Irving, TX (US)

(72) Inventors: Mirza Faizan, Irving, TX (US); Adam Mhal, Plano, TX (US); Anish Bhattacharya, Frisco, TX (US); Ayra Iftikhar, Mckinney, TX (US); Manha Sadarulanam, Plano, TX (US); Tanish Prasad, Frisco, TX (US); Vivek Maranganti, Allen, TX (US); Abdullah Kabeer, Plano, TX (US); Mirza Rizwan, Patna (IN)

(*) Notice: Subject to any disclaimer, the term of this patent is extended or adjusted under 35 U.S.C. 154(b) by 0 days.

(21) Appl. No.: 17/373,447

(22) Filed: Jul. 12, 2021

(51) Int. Cl.
| | |
|---|---|
| *H04N 5/44* | (2011.01) |
| *B60W 50/14* | (2020.01) |
| *B60W 40/08* | (2012.01) |
| *G06F 3/01* | (2006.01) |
| *B60Q 1/52* | (2006.01) |
| *B60Q 5/00* | (2006.01) |
| *G06N 3/02* | (2006.01) |
| *G06V 20/59* | (2022.01) |
| *G06V 40/16* | (2022.01) |

(52) U.S. Cl.
CPC ............. *B60W 50/14* (2013.01); *B60Q 1/52* (2013.01); *B60Q 5/00* (2013.01); *B60W 40/08* (2013.01); *G06F 3/015* (2013.01); *G06N 3/02* (2013.01); *G06V 20/597* (2022.01); *G06V 40/174* (2022.01); *B60W 2040/0827* (2013.01); *B60W 2050/143* (2013.01); *B60W 2050/146* (2013.01); *B60W 2540/221* (2020.02); *B60W 2540/229* (2020.02)

(58) Field of Classification Search
CPC ............... B60W 50/14; B60W 40/08; B60W 2040/0827; B60W 2050/143; B60W 2050/146; B60W 2540/221; B60W 2540/229; B60Q 1/52; B60Q 5/00; G06F 3/015; G06N 3/02; G06V 20/597; G06V 40/174
See application file for complete search history.

(56) References Cited

U.S. PATENT DOCUMENTS

| | | | | |
|---|---|---|---|---|
| 3,947,815 | A * | 3/1976 | Muncheryan | B60Q 1/503 340/576 |
| 2005/0163383 | A1* | 7/2005 | Kim | G06V 40/18 382/209 |
| 2006/0215244 | A1* | 9/2006 | Yosha | G02B 27/0101 359/15 |
| 2014/0204193 | A1* | 7/2014 | Zhang | G06V 40/18 348/78 |
| 2016/0001781 | A1* | 1/2016 | Fung | G16H 50/20 701/36 |
| 2016/0042240 | A1* | 2/2016 | Takeda | G06T 7/73 382/104 |
| 2017/0345276 | A1* | 11/2017 | Stoltz | G06V 20/597 |
| 2018/0260640 | A1* | 9/2018 | Lintz | G06V 20/59 |
| 2019/0100219 | A1* | 4/2019 | Jo | B60W 50/14 |
| 2021/0031687 | A1* | 2/2021 | Kim | B60R 11/04 |

* cited by examiner

*Primary Examiner* — Munear T Akki

(57) ABSTRACT

A system to generate an alert to wake a driver of a vehicle comprises at least one camera configured to sense EEG signals from the driver and a processing module, connected to the at least one camera, to process the EEG signals and to generate alarms.

7 Claims, 4 Drawing Sheets

SYSTEM TO GENERATE AN ALERT TO WAKE A DRIVER OF A VEHICLE AND A METHOD THEREOF

FIELD OF THE INVENTION

The present invention relates to a system to generate an alert to wake up a driver of a vehicle and a method thereof.

BACKGROUND OF THE INVENTION

According to the National Highway Traffic Safety Administration, every year about 100,000 police-reported crashes involve drowsy driving. These crashes result in more than 1,550 fatalities and 71,000 injuries. The real number may be much higher, however, as it is difficult to determine whether a driver was drowsy at the time of a crash.

A study by the AAA Foundation for Traffic Safety estimated that 328,000 drowsy driving crashes occur annually. That's more than three times the police-reported number. The same study found that 109,000 of those drowsy driving crashes resulted in an injury and about 6,400 were fatal. The researchers suggest the prevalence of drowsy driving fatalities is more than 350% greater than reported. Beyond the human, the toll is the economic one. NHTSA estimates fatigue-related crashes resulting in injury or death cost society $109 billion annually, not including property damage.

Not just in India, drowsy driving kills about 1,500 people and injures about 71,000 plus in the United States every year. Sixty percent of drivers, or about 168 million people, admit to driving a vehicle while drowsy in the past year. Over 100 million people have experienced falling asleep at the wheel. Current solutions to drowsy driving have proven inadequate.

Some solutions involve tracking a driver's eyes to determine whether the driver is falling asleep. More specifically, these tracking systems can determine whether a driver is looking at the road, and if he or she is not, the system can alert the driver to cause them to wake up. However, systems that track the driver's eyes fail to alert the driver soon enough. By the time the system detects that a driver is asleep, it is too late—the driver may have already lost control of the vehicle. Similar limitations exist with respect to solutions that monitor the position and/or movement of a driver's head. Some of these systems use accelerometers attached to the driver's head, for example via an earpiece, to determine whether the driver's head has dropped as a result of sleep onset. Again, however, these systems cannot detect sleep until it is too late. Furthermore, these solutions are bulky and uncomfortable to wear, causing drivers to avoid using them in the first place. In order to maintain a safe driving condition, a driver must remain awake, rather than being woken up immediately after falling asleep. For at least these reasons, a need exists for detecting and alerting a drowsy driver.

Conventionally, in order to overcome the issue of drowsiness in the driver, it is known to monitoring the user's heart rate, establishing a baseline average heart rate over a period of time, and calculating a threshold heart rate based on the baseline average heart rate. Further, the known method comprises if the threshold heart rate is less than the baseline average heart rate, detecting a drop in the user's heart rate below the threshold, and in response to detecting the drop, initiating a sleep prevention program.

Other known methods include a driver monitoring method, comprising: determining a movement of a driver based on a wearable device, controlling activation of monitoring devices provided in a vehicle based on the determining of the movement of the driver, collecting information from the monitoring devices, in response to the monitoring device being activated, and determining whether the driver is able to drive the vehicle using the collected information.

It is also known to have a vision system for a vehicle that includes a control and smart eyeglasses worn by a driver of the vehicle. The smart eyeglasses include a driver-monitoring camera that has a field of view that encompasses at least one eye of the driver when wearing the smart eyeglasses. The control includes an image processor that processes image data captured by the driver-monitoring camera to determine the drowsiness of the driver. Responsive to the determination that the driver is drowsy, the control communicates a signal to a portable device in the vehicle and the portable device in the vehicle generates an alert to the driver.

Yet another prior art suggests a method for determining vigilance of a subject, comprising the steps of: collecting eye-tracking data from a plurality of subjects; independently assessing vigilance of the subjects; using the eye-tracking data and the assessments to train a classifier, and collecting eye-tracking data from the subject and determining vigilance using the trained classifier.

However, the above-cited prior arts have drawbacks. The known devices and methods to generate an alert for the driver make use of bulky instruments or uncomfortable instruments that need to be worn by the drivers. This creates another possibility of crash driving. In fact, other devices available to wake up the driver have issues of extra cost and consuming more battery life of the vehicle due to its heavy electronic components. Thus, there is a need to have a simple system and a method to alert a drowsing driver. Above all, there is a drawback in the existing prior art that no prior art generates alarms for the outsiders. Thus, in case of the drowsiness of the driver, the alarms are generated only to wake the driver and the outside public remains unaware.

Thus, there is a need to overcome the drawbacks of these prior art. The drawbacks of prior art are overcome by the present invention, as detailed in the forthcoming sections of the present application.

OBJECTS OF THE INVENTION

The main object of the present invention is to provide a system to generate an alert to wake up a driver of a vehicle and a method thereof.

Another object of the present invention is to provide a system to display an alert message to the outside of the vehicle to warn the outsiders about the possibility of the driver sleeping in the moving vehicle and a method thereof.

Another object of the present invention is to detect if the driver is sleeping in the moving vehicle.

Another object of the present invention is to warn the outsiders and wake the driver to avoid any accidents on roads.

Another object of the present invention is to accurately detect if the driver is sleeping in the moving vehicle.

Another object of the present invention is to send real-time updates outside the vehicle if the driver is sleeping in the moving vehicle.

SUMMARY OF THE INVENTION

In order to solve the drawbacks of the prior art, the present invention provides a system to generate an alert to wake up a driver of a vehicle. According to an embodiment of the present invention, the system is configured to generate an alert to wake up a driver of a vehicle. The system comprises at least one camera configured to sense EEG signals from the driver and a processing module, connected to at least one camera, to process the EEG signals and to generate alarms.

According to an embodiment of the present invention, the system to generate an alert to wake up a driver of a vehicle comprises at least one camera configured to detect the driver's facial expressions, at least one EEG detector configured to detect EEG signals from the driver, at least one AI camera configured to detect the driver's facial expressions and enhance the driver's facial expressions using the artificial neural network; and a processing module, connected to the at least one camera, at least one EEG detector, and at least one AI camera. The processing module is configured to process the EEG signals to generate alarms. The processing module is configured to compare the detections made by the at least one camera and the AI camera to confirm the drowsiness of the driver before generating alarms. The alarms are produced inside the vehicle and/or outside the vehicle.

In some embodiments, the system to generate an alert to wake up a driver of a vehicle further comprises a screen attached outside the vehicle.

In some embodiments, the screen is connected to the processing module.

In some embodiments, the screen is configured to display a message in response to the alert generated by the processing module.

In some embodiments, the system to generate an alert to wake up a driver of a vehicle further comprises a speaker fixed inside the vehicle.

In some embodiments, the speaker is connected to the processing module.

In some embodiments, the speaker is configured to generate loud sound to wake the driver in response to the alert generated by the processing module.

In some embodiments, the at least one camera, the processing module, the screen and the speaker are connected with each other via the network.

In some embodiments, a method to generate an alert to wake up a driver of a vehicle comprises steps of placing a camera focussed on the driver's face to sense EEG signals and sending the EEG signals to a processing module. If the EEG signals indicate that the driver is sleeping, the processing module generates an alarm in speakers connected to the vehicle and sends a message to display at a screen connected outside the vehicle.

In some embodiments, a method to generate an alert to wake up a driver of a vehicle further comprises steps of if the driver is awake, reset the signals, and if the driver is not awake, continue to alert the driver with louder alert.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

Figure 1:
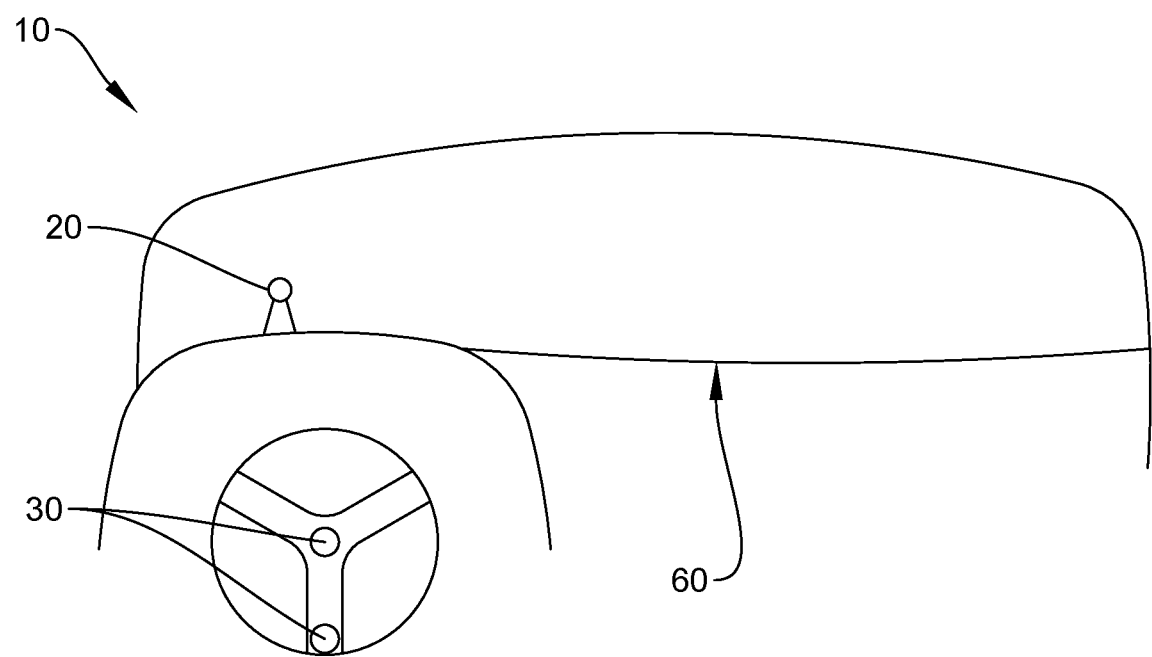
FIG. 1 is an inside view of a system installed in a vehicle to generate an alert to wake up a driver of the vehicle according to an embodiment of the present invention.

Persons skilled in the art will appreciate that elements in the figures are illustrated for simplicity and clarity and may not have been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION OF DRAWINGS

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

Embodiments of the present invention will be described below in detail with reference to the accompanying drawings.

It will be understood by those skilled in the art that the foregoing general description and the following detailed description are explanatory of the invention and are not intended to be restrictive thereof.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprise", "comprising", or any other variations thereof, are intended to cover a nonexclusive inclusion, such that a process or method that comprises a list of steps does not include only those steps but may include other steps not expressly listed or inherent to such process or method. Similarly, one or more devices or subsystems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfill the requirements of uniqueness, utility and non-obviousness.

Embodiments of the present invention will be described below in detail with reference to the accompanying drawings.

FIG. 1 is a perspective view of a system (10) to generate an alert to wake up a driver of a vehicle (60) according to an embodiment of the present invention. The system (10) to generate an alert to wake up a driver of a vehicle (60) comprises at least one camera (20) configured to sense EEG signals from the driver. In some embodiments, the vehicle (60) could be anything that is used as an instrument of conveyance. It can include any conveyance used for transporting passengers or things by land, water, or air. It can be a self-propelled conveyance that runs on tires like a motor vehicle. In some embodiment, the vehicle (60) may include, but not limited to, motor vehicles, like motorcycles, cars, trucks, buses.

According to an embodiment of the invention, the camera (20) may be any device for recording visual images in the form of photographs, film, or video signals. In some embodiments, the camera (20) may include, but not limited to, a smart camera, AI enabled cameras, or an Electroencephalogram (EEG) enabled camera. In some embodiments, the camera (20) enabled with EEG sensors may be used to visually record all the physical activities of the driver and at the same time the EEG sensors record the brain activity. In some embodiments, the EEG sensors and the camera unit (20) may be installed separately and the camera unit (20) would work as an alternative confirmation to the readings of the EG sensors. In some embodiments, the camera (20) may be AI camera connected to a storage module. When the EEG sensors give any reading of the possibility of the driver's drowsiness, the AI camera (20) would check the physical activity with the previously stored images of the drivers to provide a confirmation to the driver's drowsiness.

According to an embodiment of the present invention, the system (10) to generate an alert to wake up a driver of a vehicle (60) further comprises a speaker (30) fixed inside or outside the vehicle (60).

According to an embodiment of the present invention, the system (10) to generate an alert to wake up a driver of a vehicle (60) further comprises a processing module. In some embodiments, the processing module is connected to the at least one camera, to process the EEG signals and to generate alarms. In some embodiments, the processing module may be connected separately with both the camera (20) and the EEG sensors. In some embodiments, the processing module is connected to the AI camera (20) and the EEG sensors. In some embodiments, the processing module receives all data, signals or information in the form of digital signals, electrical signals, or any other signals capable of transferring data among the camera (20), EEG sensors and the processing module. In some embodiments, the processing module maybe, but not limited to, a central processing unit, a sensor chip, a microprocessor or any other conventional device suitable for processing information received from the camera (20) and/or the EEG sensors. In some embodiments, the processing module may be kept either inside the vehicle or outside the vehicle at remote location, and the communication of signals from the camera (20), EEG sensors and the processing module is performed via remote connection or via network, like LAN, WAN, internet, Bluetooth, wired connection or any other suitable wireless connection.

Figure 2:
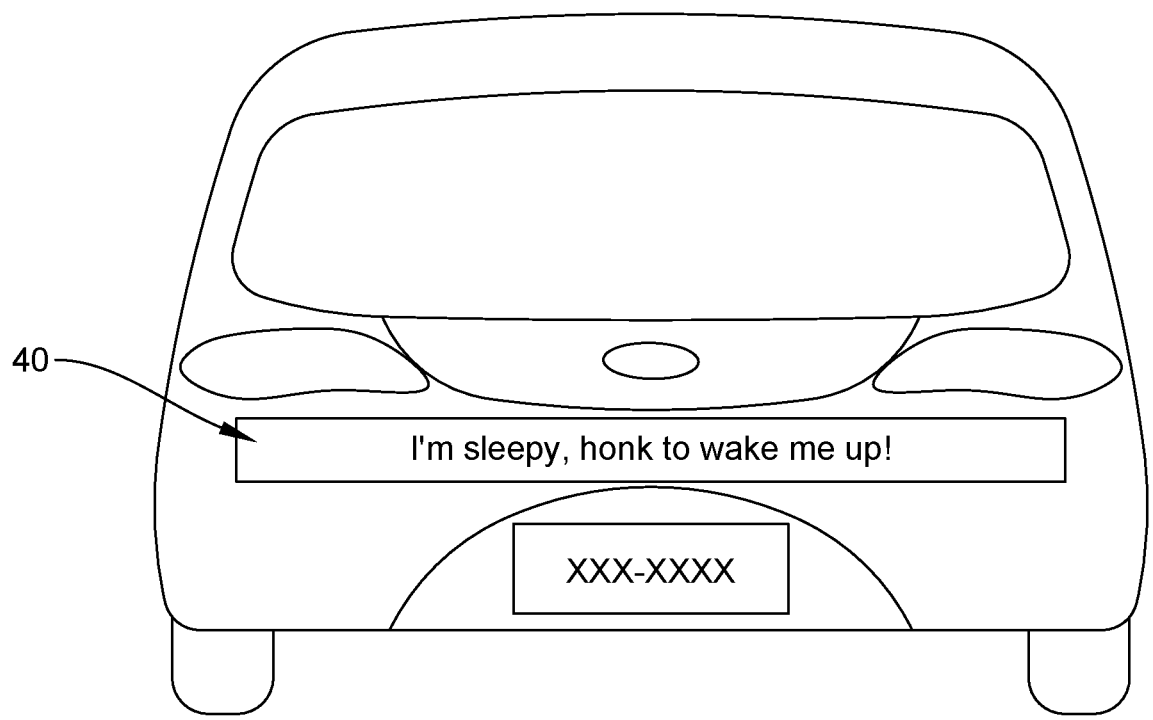
FIG. 2 is an outside view of a system installed in a vehicle to generate an alert for outsiders to warn them about the drowsiness of a driver of the moving vehicle according to an embodiment of the present invention.

FIG. 2 is a perspective view of a system (10) to generate an alert for outsiders to warn them about the drowsiness of a driver of a moving vehicle (60) according to an embodiment of the present invention. According to an embodiment of the present invention, the system (10) to generate an alert to wake up a driver of a vehicle (60) further comprises a screen (40) attached outside the vehicle (60). In some embodiments, the screen (40) may be a sticker attached outside to vehicle with lights configured to be switched ON by the processing module to warn other vehicles about the drowsiness of the driver inside the vehicle (60). In some embodiments, the screen (40) is connected to the processing module. In some embodiments, the screen (40) may be connected to the backside of the vehicle so that it is properly visible to the fellow vehicles coming from behind. In some embodiments, the screen (40) may be connected to at least one side of the vehicle so that it is properly visible to the fellow vehicles near to the vehicle (60). In some embodiments, when the processing module receive information from the camera (20) and/or from the EEG sensors, the processing module may send an alert command to the screen (40), wherein the screen is configured to display a message in response to the alert generated by the processing module. In some embodiments, the message may be formed such that it communicates to fellow vehicles to perform emergency control of their vehicles, as the driver of the moving vehicle (60) may be sleeping.

According to an embodiment of the present invention, the system (10) to generate an alert to wake up a driver of a vehicle (60) further comprises a speaker (30) fixed inside the vehicle (60). In some embodiments, the speaker (30) is connected to the processing module. The processing module sends a command or signal to the speakers to wake the driver. In response to the signal, the speaker (30) makes a loud sound. In some embodiments, the processing module may send a command or a signal to the vehicles integral electronic devices and the vehicle turns ON a light indicator in the vehicle. In some embodiments, the speaker (30) is configured to generate loud sound to wake the driver in response to the alert generated by the processing module.

Figure 3:
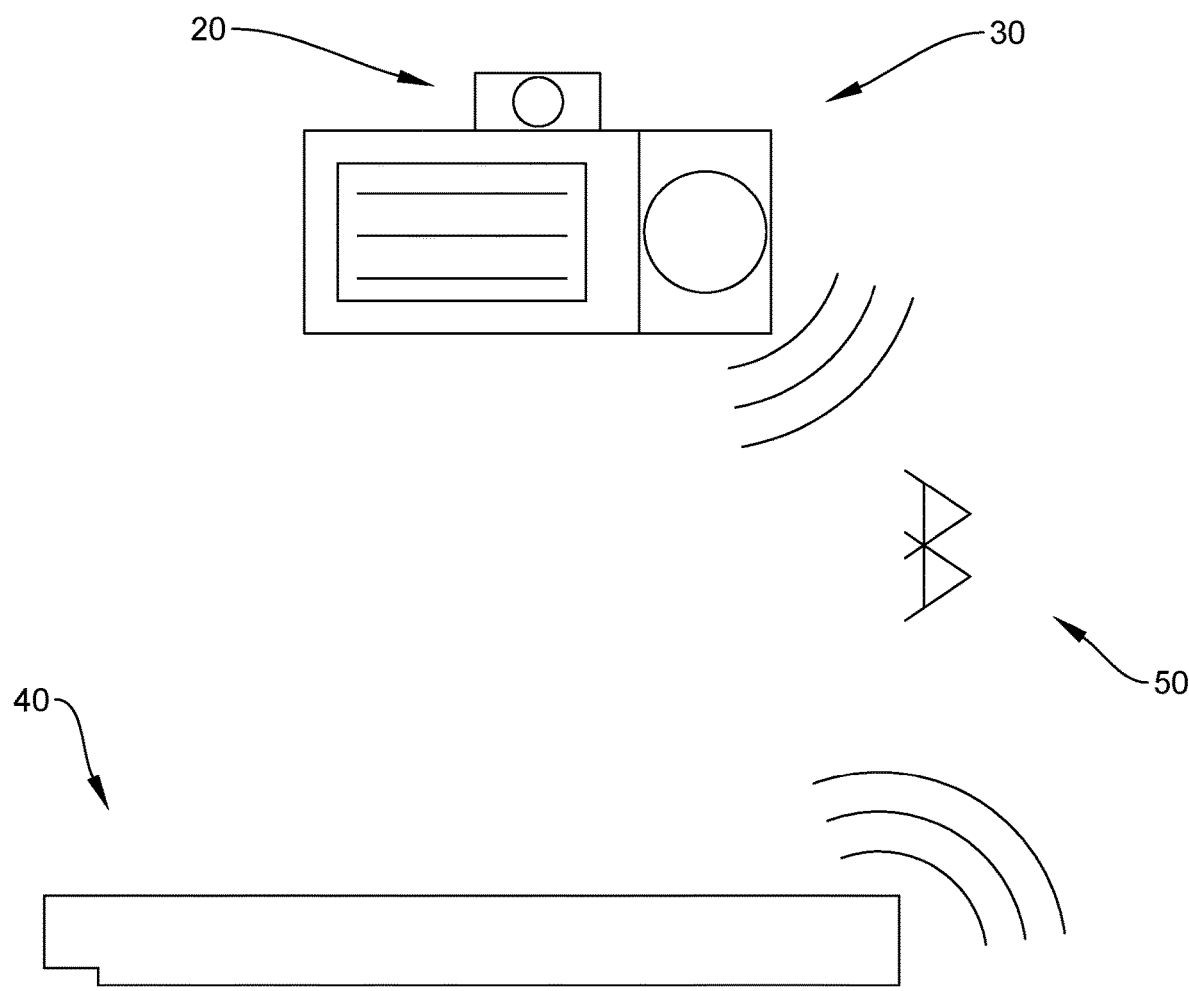
FIG. 3 is a perspective view of a system to generate an alert to wake up a driver and for outsiders to warn them about the drowsiness of a driver of a moving vehicle according to an embodiment of the present invention.

FIG. 3 is a perspective view of a system (10) to generate an alert to wake up a driver and for outsiders to warn them about the drowsiness of a driver of a moving vehicle (60) according to an embodiment of the present invention. According to an embodiment of the present invention, the system (10) to generate an alert to wake up a driver of a vehicle (60) further comprises a network (50) to form a closed network among the at least one camera (20), EEG sensors, the processing module, the screen (40) and/or the speaker (30). In some embodiments, the network (50) may be any existing secured network to connect the components of the system (10). In some embodiments, the network (50) may be any existing secured network enabled with real-time communication between the components of the system (10) to provide effective response to the signals of all the components of the system (10) comprising a camera (20), EEG sensors, the processing module, the screen (40) and/or the speaker (30).

Figure 4:
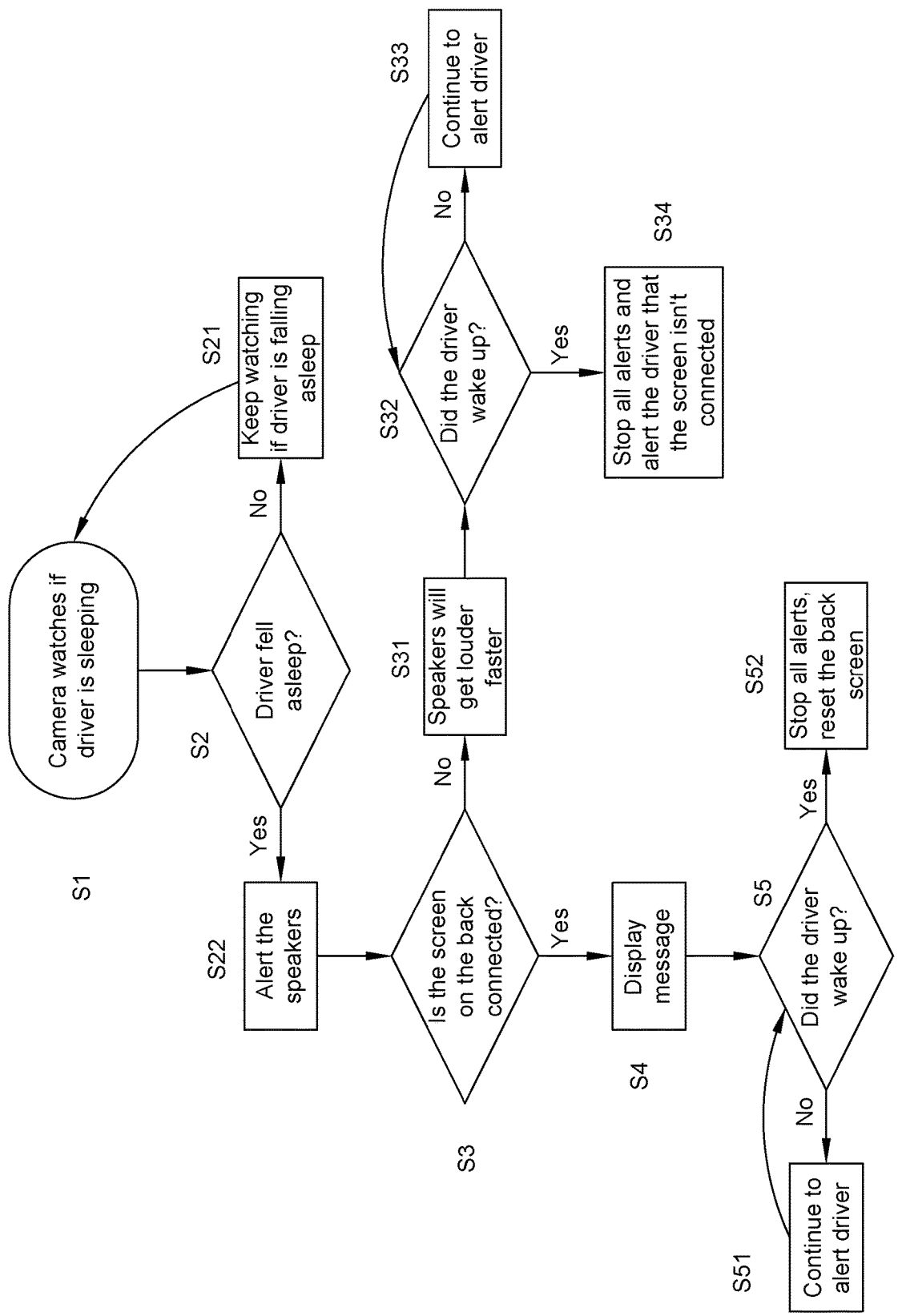
FIG. 4 is a flowchart of a method to generate an alert to wake up a driver and to warn the outsiders about the drowsiness of a driver of a moving vehicle according to an embodiment of the present invention.

FIG. 4 is a flowchart of a method to generate an alert to wake up a driver and to warn the outsiders about the drowsiness of a driver of a moving vehicle according to an embodiment of the present invention. According to an aspect of the invention, a method to generate an alert to wake up a driver of a vehicle is disclosed. In some embodiments, the method comprises steps of placing (S1) a camera focussed on the driver's face to sense EEG signals and sending the EEG signals to a processing module. In some embodiments, if the EEG signals indicate that the driver is sleeping (S2), the processing module generates an alarm (S22) in speakers connected to the vehicle and send (S4) a message to display at a screen connected outside the vehicle. In some embodiments, if the driver is not sleeping, the camera and/or the EEG sensors continue to observe (S21) the driver.

In some embodiments, the processing module will check if the screen (S3) is connected to the system.

In some embodiments, if the screen is not connected, the processing module gives a signal to the speakers to produce louder alarms (S31). In the next step (S32), the processing module will again check if the driver is awake after the loud alarms. If the driver is not awake, then the signals will be sent to continue to wake the driver (S33). On the other hand, if the driver is awake, reset the signals (S34) or stop all alerts and inform the driver that the screen is not connected.

In some embodiments, on the other hand, if the screen is connected, the processing module sends (S4) the signals to the screen to display a message to warn fellow vehicles. The processing module again sends (S5) signals to the camera and/or EEG sensors to check now if the driver is awake. If the driver is awake, the next step (S52) is to stop all alerts and rest the back screen. If the driver is not awake, continue (S51) to alert the driver.

Moreover, the actions of any components in the block diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the present subject matter, any limitations arising on account thereto, are not intended. As would be apparent to a person in the art, various working modifications may be made to the method in order to implement the inventive concept as taught herein. The drawings and the foregoing description give examples of embodiments.

What is claimed is:

1. A system to generate an alert to wake up a drowsy driver of a moving vehicle, said system comprises:
   at least one camera configured to detect driver's facial expressions;
   at least one Electroencephalograph (EEG), detector configured to detect EEG signals from the driver;
   at least one Artificial Intelligence (AI) camera configured to detect the driver's facial expressions and enhance the driver's facial expressions using artificial neural network;
   a processing module, connected to the at least one camera, at least one EEG detector and at least one AI camera;
   wherein the processing module is configured to process the EEG signals,
   wherein the at least one Camera and the at least one AI camera take pictures of driver's face and send the pictures to processing module to start comparison of driver's face with a database of pre-stored training pictures after receiving signal from EEG, and
   wherein the processing module is configured to compare the detections made by at least one camera and the at least one AI camera to confirm the drowsiness of the driver,
   wherein the system generates an alarm after receiving the confirmation of driver's drowsiness,
   wherein the alarms are produced inside the vehicle and/or outside the vehicle.

2. The system to generate the alert to wake up the driver of the vehicle as claimed in claim 1 further comprises a screen and a speaker attached outside the vehicle.

3. The system to generate the alert to wake up the driver of the vehicle as claimed in claim 2 wherein the screen and the speaker are connected to the processing module.

4. The system to generate the alert to wake the driver of the vehicle as claimed in claim 3 wherein the screen is configured to display a message and the speaker is configured to make a louder noise outside the vehicle in response to the alert generated by the processing module.

5. The system to generate the alert to wake the driver of the vehicle as claimed in claim 1 further comprises a speaker fixed inside the vehicle.

6. The system to generate the alert to wake up the driver of the vehicle as claimed in claim 5, wherein the speaker that fixed inside the vehicle is connected to the processing module.

7. The system to generate the alert to wake the driver of the vehicle as claimed in claim 6, wherein the speaker that fixed inside the vehicle is configured to generate loud sound to wake the driver in response to the alert generated by the processing module.

* * * * *